United States Patent
Van 'T Hof et al.

(10) Patent No.: US 11,291,586 B2
(45) Date of Patent: Apr. 5, 2022

(54) EARPLUG AND METHOD FOR ATTENUATING SOUND

(71) Applicant: DYNAMIC EAR COMPANY B.V., Delft (NL)

(72) Inventors: Pieter Gerard Van 'T Hof, Delft (NL); Joost Leendert Lodder, Delft (NL)

(73) Assignee: Sonova AG, Staefa (CH)

( * ) Notice: Subject to any disclaimer, the term of this patent is extended or adjusted under 35 U.S.C. 154(b) by 372 days.

(21) Appl. No.: 16/471,303

(22) PCT Filed: Dec. 19, 2017

(86) PCT No.: PCT/NL2017/050847
§ 371 (c)(1),
(2) Date: Jun. 19, 2019

(87) PCT Pub. No.: WO2018/117821
PCT Pub. Date: Jun. 28, 2018

(65) Prior Publication Data
US 2019/0321230 A1    Oct. 24, 2019

(30) Foreign Application Priority Data

Dec. 20, 2016 (NL) ..................... 2018029

(51) Int. Cl.
*A61F 11/08* (2006.01)
(52) U.S. Cl.
CPC ......... *A61F 11/08* (2013.01); *A61F 2011/085* (2013.01)
(58) Field of Classification Search
CPC ... A61F 11/06–12; H04R 1/10; H04R 1/1016; H04R 1/1058; H04R 1/1066;
(Continued)

(56) References Cited

U.S. PATENT DOCUMENTS

| 4,540,063 A | * | 9/1985 | Ochi ................. A61F 11/08 128/867 |
| 4,852,683 A | | 8/1989 | Killion |

(Continued)

FOREIGN PATENT DOCUMENTS

| CN | 1422140 A | 6/2003 |
| EP | 1046382 A1 | 10/2000 |
| EP | 2439734 A1 | 4/2012 |
| WO | 01/76520 A1 | 10/2001 |
| WO | 2011/078659 A1 | 6/2011 |
| WO | 2016/010431 A1 | 1/2016 |

OTHER PUBLICATIONS

English translation Notification of the First Office Action dated Jul. 28, 2020 issued in corresponding Chinese Patent Application No. 2017800862537 (9 pgs.).

(Continued)

*Primary Examiner* — Michelle J Lee
(74) *Attorney, Agent, or Firm* — Pillsbury Winthrop Shaw Pittman, LLP

(57) ABSTRACT

An earplug and method for attenuating sound. An acoustic canal extends straight through a housing to guide the sound inside an ear canal. The acoustic canal comprises a canal section dimensioned to fit at least partially inside the ear canal. The canal section ends at one side in a first exterior opening to let the sound into the ear canal. Another side of the canal section transitions into a first resonance volume with a relatively wide diameter. A second resonance volume ends at one side in a second exterior opening and, the other side being separated from the first resonance volume by a sound attenuating mesh. This provides resonance cavities that compensate attenuation of the mesh over a wide range of high frequencies.

12 Claims, 4 Drawing Sheets

(58) Field of Classification Search
CPC ...... H04R 1/1083; H04R 1/1091; H04R 1/20; H04R 1/22; H04R 25/00; H04R 25/02; H04R 25/48; H04R 25/60; H04R 25/603; H04R 25/607; H04R 25/609; H04R 25/65; H04R 25/652; H04R 25/656; H04R 25/658; H04R 2225/57
See application file for complete search history.

(56) References Cited

U.S. PATENT DOCUMENTS

| | | | |
|---|---|---|---|
| 5,113,967 A | | 5/1992 | Killion et al. |
| 6,148,821 A | * | 11/2000 | Falco ............... H04R 1/1016 128/864 |
| 2002/0179365 A1 | * | 12/2002 | Meussen ............. A61F 11/08 181/135 |

OTHER PUBLICATIONS

Search Report dated Jun. 15, 2017 issued in corresponding Netherlands Patent Application No. 2018029 (8 pgs.).
International Preliminary Report on Patentability dated Jun. 25, 2019 issued in corresponding International Application No. PCT/NL2017/050847 (7 pgs.).
Written Opinion of the International Searching Authority dated Jun. 3, 2018 issued in corresponding International Patent Application No. PCT/NL2017/050847.
International Search Report dated Jun. 3, 2018 issued in corresponding International Patent Application No. PCT/NL2017/050847.

* cited by examiner

EARPLUG AND METHOD FOR ATTENUATING SOUND

CROSS-REFERENCE TO RELATED APPLICATIONS

This is the U.S. National Stage of PCT/NL2017/050847, filed Dec. 19, 2017, which in turn claims priority to Netherlands Patent Application No. 2018029, filed Dec. 20, 2016, the contents of each of these applications being incorporated herein by reference in their entireties.

TECHNICAL FIELD AND BACKGROUND

The present disclosure relates to an earplug and method for attenuating sound.

Earplugs provide a simple way to dampen sound from an outside surroundings to an ear canal. Acoustic attenuation can be achieved for example by an acoustic dampening element such as a membrane or mesh disposed in an acoustic canal through the earplug. A mesh has a desired property that it can allow ventilation or equilibration of air and water there through. However, the acoustic transfer function of a mesh typically shows increasing attenuation at higher frequencies. This may be perceived by the user as an occlusion effect, which is undesirable.

Excessive dampening at high frequencies can be (partially) compensated by providing a canal with a specifically tuned resonance frequency. However to provide the resonance at a desired frequency range may require a long canal, typically around a quarter wavelength of the sound. The canal may be folded, but this may leads to a more complicated construction and less adaptability, e.g. tuning of the resonance to a specific user. Furthermore, creating a resonance at one frequency can have the effect of even further lowering sound levels at adjacent frequencies.

It is thus desired to provide a compact ventilating earplug of simple construction which provides attenuated sound with minimal occlusion effect over an extended range of frequencies.

SUMMARY

Aspects of the present disclosure provide an earplug and method for attenuating sound from an outside surroundings to an ear canal. The earplug comprises a housing with an ear tip configured to form an acoustic seal with the ear canal. An acoustic canal extends straight through the housing to guide the sound from the outside surroundings to inside the ear canal. The acoustic canal comprises a canal section having a first diameter that is dimensioned to fit at least partially inside the ear canal. The canal section ends at one side in a first exterior opening that is in use directed to let the sound through the earplug into the ear canal. Another side of the canal section transitions into a first resonance volume. The first resonance volume starts from an end of the canal section with a second diameter that is wider than the first diameter. The acoustic canal further comprises a second resonance volume ending at one side in a second exterior opening. The second exterior opening is in use directed to the outside surroundings for receiving the sound. Another side of the second resonance volume is separated from the first resonance volume by a sound attenuating mesh bounding one side of each of the resonance volumes. The resonance volumes form part of respective resonance cavities separated by the mesh. The resonance cavities provide resonance peaks that (partially) compensate attenuation of the mesh in a resonance frequencies range above one kilohertz.

By providing a straight canal, the earplug can be of relatively simple construction. The straight canal may also provide less frequency dependence compared to a folded canal and also improve ventilation of the ear canal in combination with the mesh. By providing a canal section that connects to a relatively wide resonance volume, the combination may act similar to a Helmholtz resonator wherein the resonance frequency can be decreased by increasing the volume rather than extending the length of the canal. In this way the earplug can be more compact without requiring a complicated channel. The resonance can also be easily tuned by adapting the volume without having to extend a length of the earplug. By providing a second resonance volume, a distinct resonance peak can be achieved which extends the frequency range for compensating the mesh attenuation above one kilohertz. By providing the mesh between the resonance volumes, each cavity is bounded while at the same time providing attenuation through the acoustic canal. This further simplifies construction. By providing the second resonance volume with an exterior opening facing the outside surroundings, especially high frequency sound can more easily enter the acoustic canal of the earplug. This secondary resonance volume might be placed in the concha of the ear, thus filling the concha opening partially. Optional openings to the circumference of the secondary resonance volume may improve directional hearing, thus further improving the acoustic properties of the earplug. All features combined may thus provide a compact ventilating earplug of simple construction which provides attenuated sound with minimal occlusion effect over an extended range of frequencies.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1:
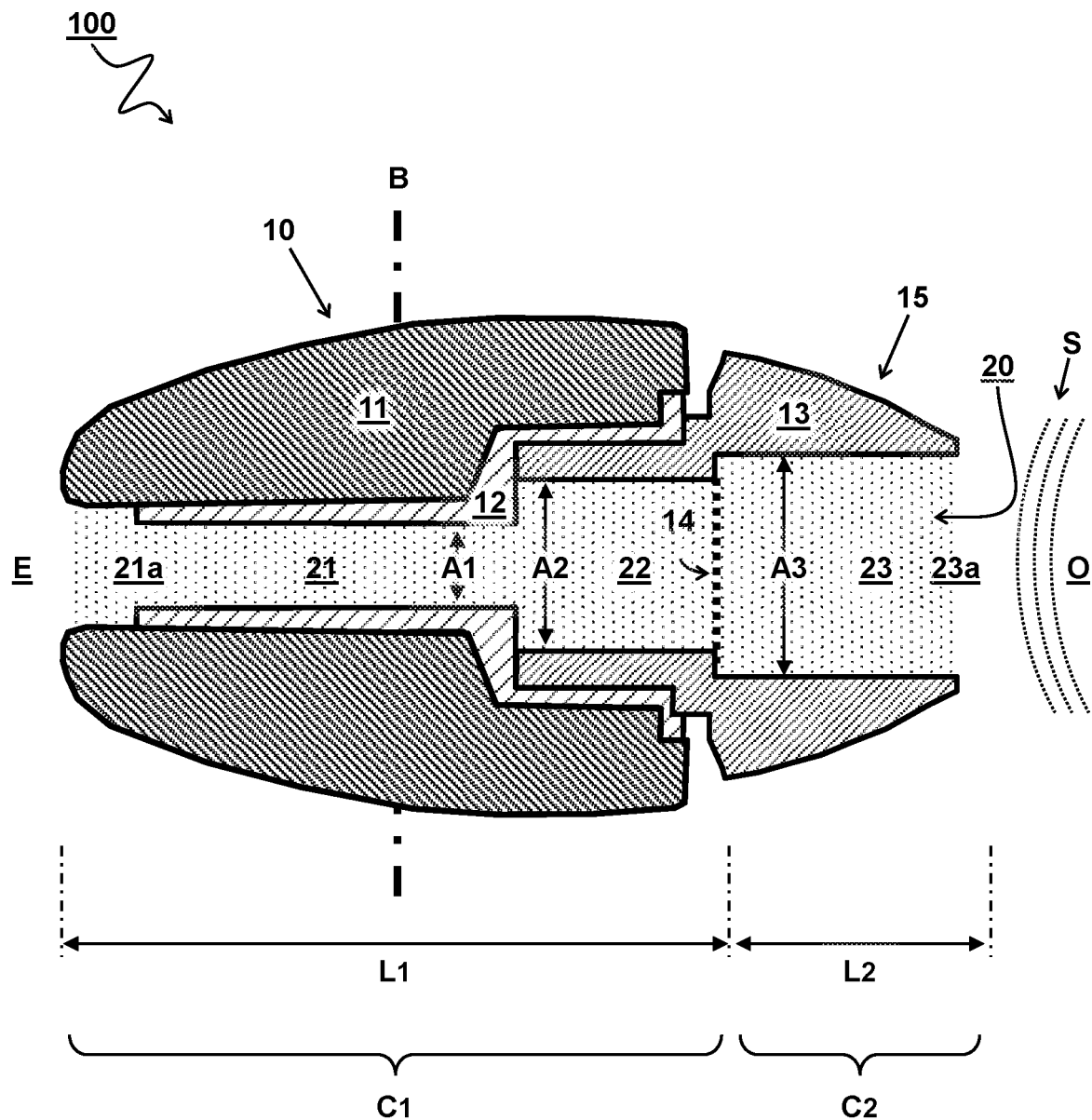
FIG. 1 schematically illustrates a cross-sectional view of an embodiment for the earplug.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be understood that when a connection between structures or components is described, this connection may be established directly or through intermediate structures or components unless specified otherwise.

FIG. 1 schematically illustrates a cross-sectional view of an embodiment for an earplug 100 for attenuating sound S from an outside surroundings O to an ear canal E.

Typically, the earplug 100 comprises a housing 10 with an ear tip 11 configured to form an acoustic seal B with the ear canal E. An acoustic canal 20 extends through the housing 10 to guide the sound S from the outside surroundings O to inside the ear canal E.

In one embodiment, the acoustic canal 20 comprises a canal section 21 having a first diameter A1 that is dimensioned to fit at least partially inside the ear canal. The canal section 21 ends at one side in a first exterior opening 21a that is in use directed to let the sound S into the ear canal. Another side of the canal section 21 transitions into a first resonance volume 22. The first resonance volume 22 may be defined as starting from an end of the canal section 21 at a position of a second diameter A2 where it gets wider than the first diameter A1.

In the embodiment shown, the canal section 21 is a straight canal between the ear canal E and the first resonance volume 22. The canal section 21 is typically formed by a relatively narrow first tubular part 12 extending partially through the housing 10. Preferably, the first tubular part 12 is covered by an exterior part forming the ear tip 11. For example, the ear tip 11 comprises a flexible exterior configured to adapt to its form to an entry of the ear canal E, e.g. a viscoelastic tip. For example, the ear tip 11 comprises thermoplastic elastomer TPE or silicone. Alternatively, or in addition, the ear tip 11 comprises a custom molded earplug, e.g. otoplastics.

Typically, the canal section 21, first resonance volume 22, and/or second resonance volume 23 have a cylindrical shape. Preferably, the cylindrical sections line up along a straight line through the earplug, e.g. having a common central axis. Alternatively, other shapes may be used, e.g. elliptical, square triangular, etcetera, and/or the central axis may be shifted between sections.

In a preferred embodiment, the first resonance volume 22 and/or second resonance volume 23 is formed in a relatively wide second tubular part 13. These parts can be wider because they need not fit in the ear canal. For example, the second tubular part 13 forms the second resonance volume 23 as an open volume with the second exterior opening 23a configured to catch sound S from the outside surroundings O and guide them into the earplug 100.

In one embodiment, as shown, the second resonance volume 23 is formed by a surrounding mantle section ending at one side with the mesh 14 and at the opposite side in an opening to the outside surroundings O. In another or further embodiment (not shown) the mantle section comprises one or more additional side openings. For example, the side openings can be holes in the mantle section or slits extending from the central opening 23a into the mantle section. The holes at the side may allow sound to enter, e.g. bouncing from the concha of the ear, to improve directional hearing of a user wearing the ear plug.

In a preferred embodiments, the earplug comprises a sound attenuating element, such as a mesh or mesh-like structure 14 in the acoustic canal 20. It will be understood that the mesh may comprise any sound attenuating surface or foil with a structure defining microscopic holes distributed over the surface for filtering sound waves there through. The microscopic holes or slits typically have a small cross-section diameter, preferably less than two hundred micrometer, e.g. between ten and hundred micrometer. For example, precision woven meshes for use in acoustic applications can be made wires woven together. Alternatively, mesh-like structures may be produced by injection molding, e.g. comprising micro-slits or holes. The mesh is typically made of strong nylon, metal, PE or PET. After providing the mesh in the desired dimensions, it is typically connected to a carrier part such as the second tubular part 13 to give it support. For example a connection between the mesh and the carrier may comprise gluing, ultrasonic welding or injection molding the part around the mesh. In some cases, the second tubular part 13 may be constructed as one piece integral with the mesh 14, e.g. by molding the part together with the mesh.

In the embodiment shown, a surface of the mesh is transverse to a length of the acoustic canal 20. In another embodiment (not shown), the mesh 14 can be tilted, e.g. wherein a normal vector to a surface of the mesh is at an angle with respect to a centerline of the acoustic canal 20. Tilting the mesh at an oblique angle may increase its effective surface e.g. for exchange of water and air there through. For example, the mesh can be tilted by at least twenty degrees, e.g. wherein the normal vector of the mesh surface is at an angle between forty and sixty degrees with respect to the centerline of the acoustic canal. In some embodiments, the second tubular part 13 comprises the mesh 14 separating the first resonance volume 22 and second resonance volume 23. The mesh 14 can also be provided elsewhere.

In some embodiment, as shown, the acoustic canal 20 comprises an optional second resonance volume 23 ending at one side in a second exterior opening 23a. Preferably, the second exterior opening 23a is in use directed to the outside surroundings for receiving the sound S. Preferably, the second exterior opening 23a faces in an opposite direction with respect to the first exterior opening 21a. For example, the acoustic canal 20 is directed along a straight line between the second exterior opening 23a and the oppositely facing first exterior opening 21a. Advantageously, the second resonance volume 23 may be separated from the first resonance volume 22 by the sound attenuating mesh 14. Accordingly, the mesh 14 can act as a boundary at one side of each of the resonance volumes 22,23. In this way the resonance volumes 22,23 may form part of respective resonance cavities C1,C2 separated by the mesh 14.

Preferably, a combined length L1 of the canal section 21 and first resonance volume 22 is relatively short, For example, the length L1, measured between the mesh 14 and an edge of the first exterior opening 21a is less than twenty millimeter, preferably less than eighteen, seventeen, or sixteen millimeter, e.g. between one and two centimeters.

The canal section is preferably narrow to fit in the ear canal. For example, the canal section 21 has a diameter A1 in a range between one and five millimeter, preferably between one-and half and four millimeter, or between two and three millimeter. Preferably, the canal section 21 is relatively short to provide a compact earplug yet long enough to fit with sufficient length in the ear canal. For example, the canal section 21 has a length in a range between five and twelve millimeter, preferably between eight and eleven millimeter.

The first resonance volume 22 may e.g. be defined between the mesh 14 up to but not including the canal section 21. To provide sufficient volume, a diameter A2 of the first resonance volume 22 is preferably larger than a diameter A1 of the canal section 21, e.g. at least by a factor one-and-half, two, two-and-half, or more, e.g. up to a factor three, four, or five. For example, the first resonance volume 22 has a diameter A2 in a range between three-and-half and five-and-half millimeter, preferably between four and five millimeter, e.g. four-and-half millimeter. Alternatively, or in addition, a cross-sectional area of the first resonance volume 22 is larger than a cross-sectional area of the canal section 21, e.g. by a factor two, three, four, five, or more. Preferably, a volume of the first resonance volume 22 is larger than a volume of the canal section 21, e.g. by a factor of one-and-half, two, or more, e.g. up to a factor three or four. For example, the first resonance volume 22 is preferably between thirty and hundred fifty cubic millimeter, e.g. more than fifty cubic millimeter.

The second resonance volume 23 may be defined between the mesh 14 up to the edge of the second exterior opening 23a. In some embodiments, the second resonance volume 23 has a diameter A3 that is even larger than a diameter A2 of the first resonance volume 22, e.g. larger by a factor 1.1 or 1.2, or more, e.g. up to a factor 1.5. The larger diameter may provide a relatively large entry for receiving sound S. For example, the second resonance volume 23 has a diameter A3 in a range between 4.5 and 6.5 millimeter, preferably between five and six millimeter, e.g. five-and-half millimeter. The second resonance volume 23 can also be relatively large, e.g. with a volume between hundred and two hundred cubic millimeter, e.g. hundred fifty cubic millimeter. In some cases, the second resonance volume 23 may be larger than the first resonance volume 22, e.g. by a factor 1.2, 1.3, or more, e.g. up to a factor two. It is noted that the larger diameter A3 at the exterior opening 23a may cause a relatively higher resonance frequency.

Figure 2A:
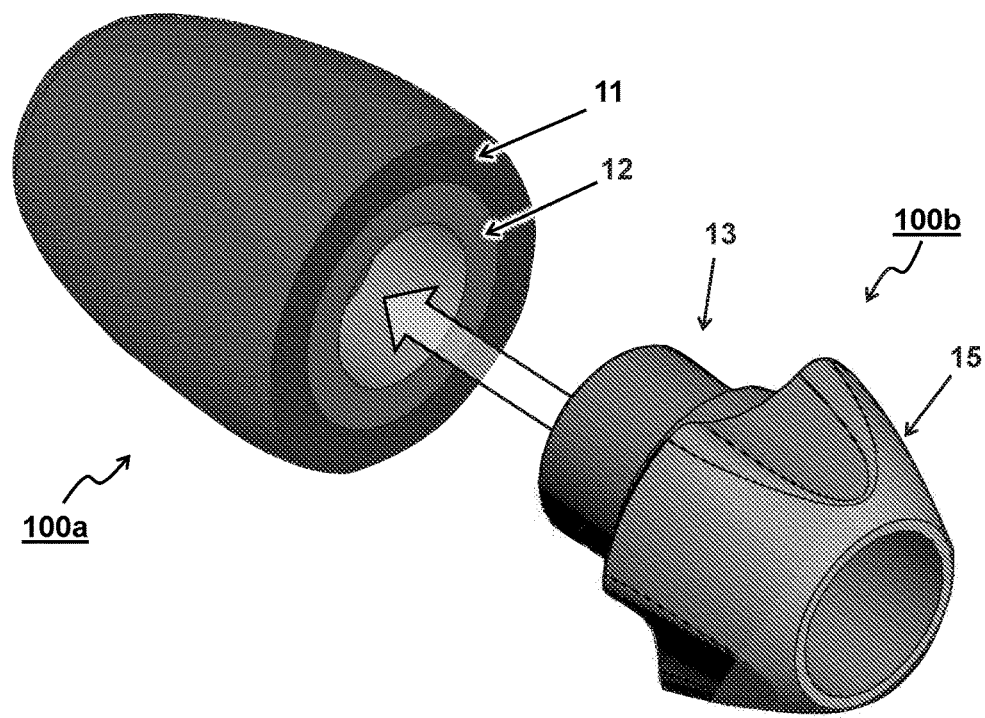
FIG. 2A schematically illustrates an isometric view of an embodiment for the earplug comprising two parts.
Figure 2B:
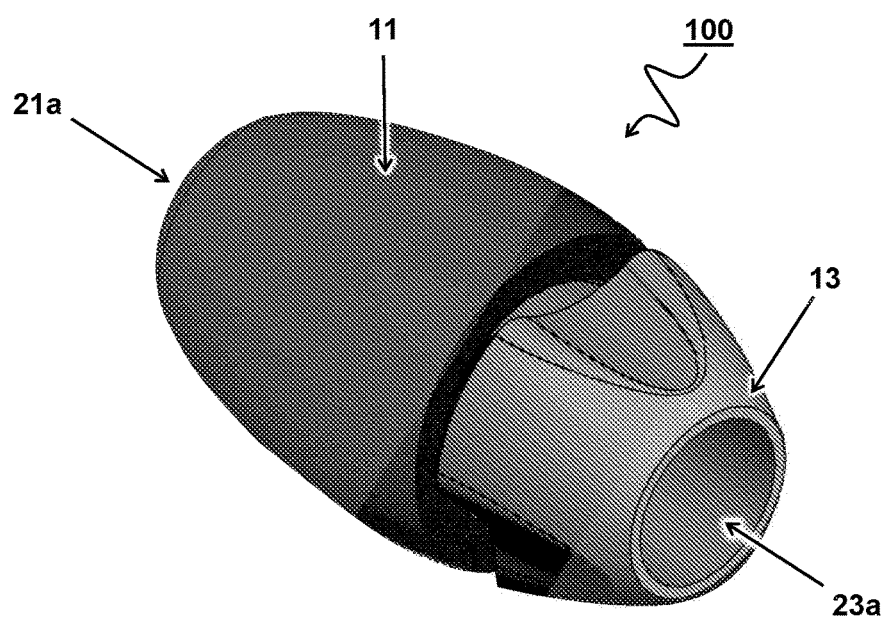
FIG. 2B schematically illustrates the parts brought together to form the earplug.

FIG. 2A schematically illustrates an isometric view of an embodiment for the earplug comprising two parts. FIG. 2B schematically illustrates the parts brought together to form the ear plug.

In one embodiment, the earplug 100 comprises at least two parts 100a,100b fitting together. For example, the first part 100a of the earplug comprises a first tubular part 12 covered at its outer hull by material forming the ear tip 11. The second part 100b of the ear plug may comprise a second tubular part 13, wherein the first tubular part 12 and the second tubular part 13 fit together. For example, a shape fitting wherein the outer diameter of a section of the second tubular part 13 is slightly higher than the inner diameter of the corresponding section of the first tubular part 12. Accordingly, the first tubular part 12 can have a widened section configured to receive a section of the second tubular part 13 forming the first resonance volume 22. In another embodiment (not shown) the fitting parts may be reversed, e.g. a part of the first part 100a of the earplug can fit into the second part 100b of the ear plug.

In some embodiments, as shown, the second part 100b of the ear plug comprise a finger gripping portion with two, three, or more depressions to facilitate gripping the ear plug with two, three, or more finger.

In one embodiment, two parts of the earplug fit together with a controllable distance defining a variable volume of the first resonance cavity C1. In this way, the resonance frequency may be tuned. For example, the parts may fit together with a bayonet or screw connection (not shown) wherein a turning of one part with respect to the other determines the resonance volume and frequency. Alternatively, a simple sliding connection can be provided, e.g. wherein the parts fit tightly together. By allowing user-control over the volume of the resonance cavity C1, the corresponding resonance frequency can be adapted to a specific ear shape or preference of the user.

Figure 3:
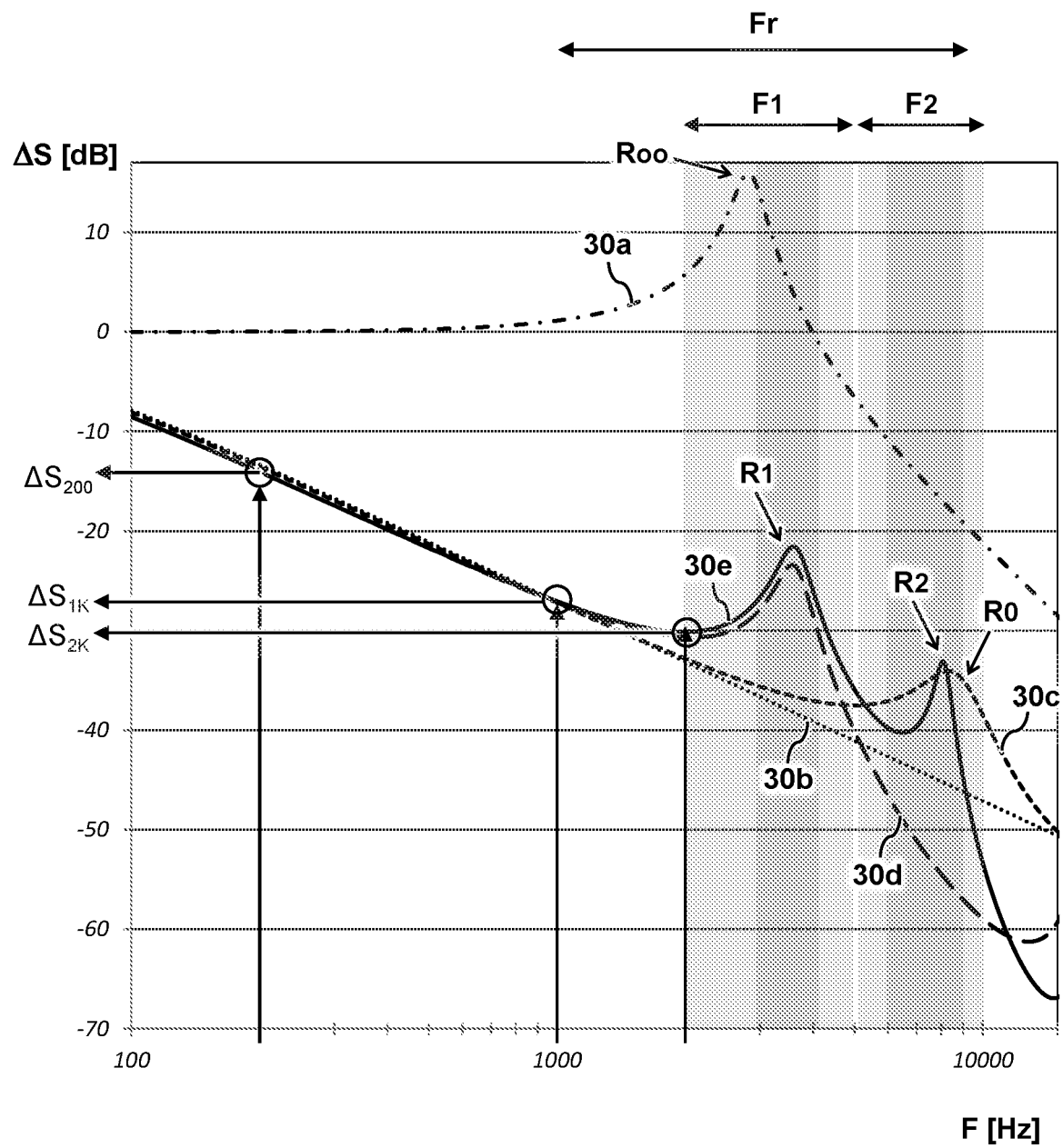
FIG. 3 shows model calculations of frequency dependent relative sound levels to illustrate the effects provided by different parts forming the earplug.
Figure 4A:
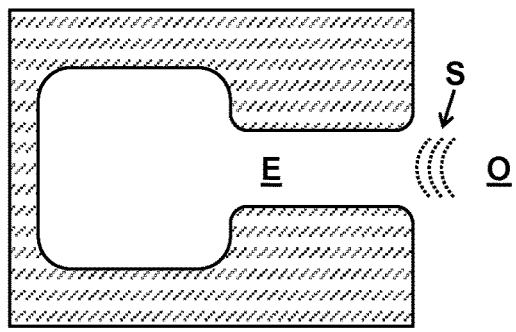
FIGS. 4A-4E illustrate parts of the earplug used in the model calculations of FIG. 3.
Figure 4B:
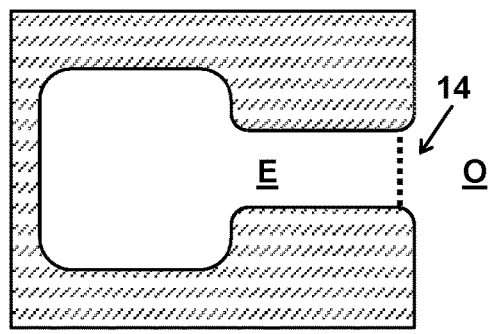
Figure 4C:
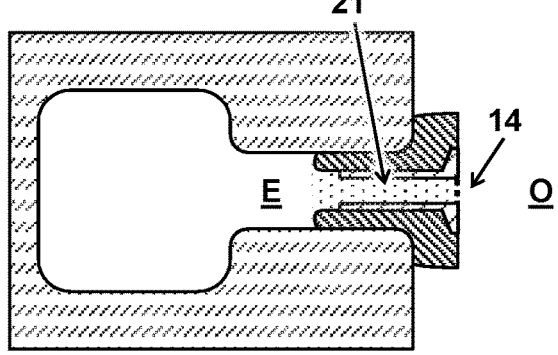
Figure 4D:
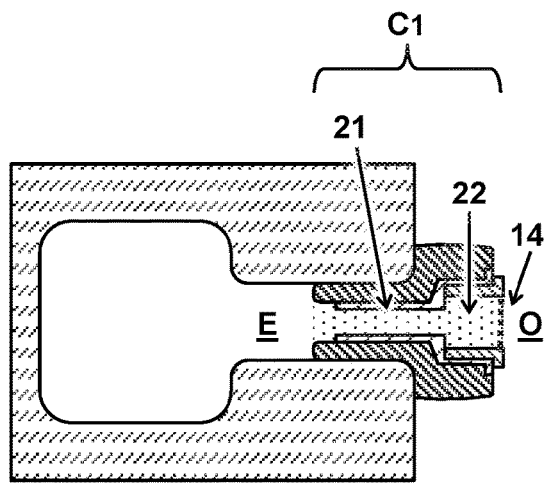
Figure 4E:
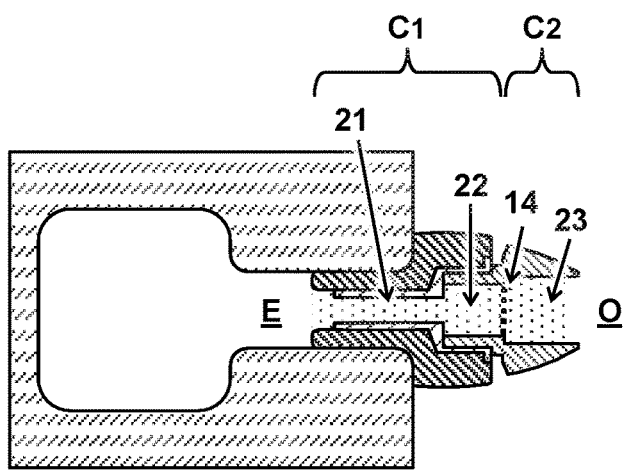

FIG. 3 shows model calculations of frequency (F) dependent (relative) sound levels ($\Delta$S) to illustrate effects provided by different parts forming the earplug. Correspondingly, FIGS. 4A-4E illustrate the parts or embodiments of an earplug used in the model calculations of FIG. 3.

Curve 30a illustrates a modelled open ear response of a human ear without earplug. See also FIG. 4A. The curve shows a natural resonance peak Roo extending approximately between one and four kilohertz. Such resonance may typically depend on the shape and dimensions of the ear canal. In some cases the resonance can be useful in emphasizing some higher frequencies that may be part of human speech.

Curve 30b illustrates a modelled response of attenuation provided by only the mesh 14. See also FIG. 4B. Typically, the mesh 14 provides lowering sound levels (or increasing attenuation $-\Delta$S) for increasing frequencies F. In some embodiments, the mesh 14 is configured to provide sufficient attenuation of the sound S at two hundred Hertz $\Delta S_{200}$ between ten and twenty-five decibel. In other or further embodiments, the mesh 14 is configured to provide attenuation of the sound S at one kilohertz $\Delta S_{1K}$ between twenty and thirty five decibel.

Curve 30c illustrates a modelled response of attenuation provided by the mesh 14 in combination with only a straight canal section 21. See also FIG. 4C. Comparing curves 30b and 30c illustrates that addition of the canal section 21 causes a resonance peak R0 which partially compensates attenuation of the mesh 14 but at relatively high frequencies above five kilohertz.

Curve 30d illustrates a modelled response of attenuation provided by the mesh 14 in combination with the first resonance cavity C1 formed by the canal section 21 and the first resonance volume 22. See also FIG. 4D. Comparing curves 30c and 30d illustrates that addition of the first resonance volume 22 to the canal section 21 has the effect of shifting the resonance peak of the combined first resonance cavity C1 from an original peak R0 to a shifted peak R1 at a lower frequency.

The position of the first resonance peak R1 may be controlled by adapting the volume of the first resonance volume 22, e.g. with a larger volume or wider cross-section section A2 resulting in a lower frequency of the first resonance peak R1. In this way, an overall length of the earplug can be kept within a desired range. The position of the first resonance peak R1 may also be controlled by adapting a length of the canal section 21, e.g. with a longer canal resulting in a lower frequency of the first resonance peak R1. However this may lead to a long canal and too large ear plug for the desired frequency shift. In some embodiments, this construction provides desired compensation for attenuation of the mesh 14 at frequencies between one and four kilohertz. However, it is noted that the sound level may actually be decreased for frequencies above four kilohertz.

Curve 30e illustrates a modelled response of attenuation provided by the mesh 14 in combination with the first resonance cavity C1 and the second resonance cavity C2 formed by the second resonance volume 23. See also FIG. 4E. Comparing curves 30d and 30e illustrates that addition of the second resonance volume 23 has the effect of increasing the sound levels or decreasing the attenuation also at higher frequencies, e.g. between four and ten kilohertz. Accordingly, the attenuation of the mesh 14 may be partially compensated over a relatively wide range of frequencies.

This illustrates that the resonance cavities C1,C2 of the earplug can provide resonance peaks R1,R2 that at least partially compensate attenuation of the mesh 14. In other words, the sound S is less attenuated around the resonance peaks R1,R2 than it would be in absence of the resonance cavities. Advantageously, the acoustic canal can be configured to provide at least two distinct resonance peaks R1,R2 that partially counteract attenuation $-\Delta S$ of the sound S by the mesh 14 in respective frequency ranges around the resonance peaks R1,R2.

Preferably, the compensation takes place in a resonance frequencies range Fr above one kilohertz. In one embodiment, the maxima of the resonance peaks R1,R2 are in a frequency range Fr above two kilohertz, preferably above three kilohertz. In another or further embodiment, the maxima of the resonance peaks R1,R2 are in a frequency range Fr below ten kilohertz, preferably below nine kilohertz.

To cover a wide frequency range it is preferred that, the maxima of the resonance peaks R1,R2 are at least two kilohertz apart, preferably at least three or four kilohertz. Furthermore, it is preferably that each of the resonance peaks R1,R2 covers a relatively wide range. For example a full width of the resonance peak at $-6$ dB from its maximum is at least five hundred hertz, preferably more than one kilohertz.

Accordingly, the resonance frequencies may cover a range at least between two and six kilohertz, preferably a wider range, e.g. between one kilohertz up to seven, eight, nine, or ten kilohertz. Accordingly, the resonance peaks R1,R2 are adapted to lower high-frequency attenuation of the sound S above one kilohertz.

Preferably, the sound level is relatively constant over a range of frequencies. For example, in some embodiments, a difference between attenuation of sound S at two kilohertz $-\Delta S_{2K}$ compared to attenuation at one kilohertz $-\Delta S_{1K}$ is less than five decibel [dB], preferably less than four or three decibel.

In one embodiment, e.g. according to FIG. 1, the canal section 21 and the first resonance volume 22 are configured to form, in combination, a first resonance cavity C1 with a first resonance peak R1 for the sound S in a first frequency range F1 between two and five kilohertz, preferably between three and four kilohertz. For example, the first resonance cavity C1 is adapted to create the first resonance peak R1 just above a resonance Roo of an open ear response 30a. In another or further embodiment, the second resonance volume 23 is configured to form a second resonance cavity C2 with a second resonance peak R2 for the sound S in a second frequency range F2 between five and ten kilohertz, preferably between six and nine kilohertz.

In some aspects, the figures illustrate an earplug 100 and corresponding method for attenuating sound S from an outside surroundings O to an ear canal E. A housing 10 is provided with an ear tip 11 to form an acoustic seal B with the ear canal E. An acoustic canal 20 extends straight through the housing 10 to guide the sound S from the outside surroundings O to inside the ear canal E. The acoustic canal 20 comprises a canal section 21 having a first diameter A1 that fits at least partially inside the ear canal. The canal section 21 ends at one side in a first exterior opening 21a that lets the sound S into the ear canal. Another side of the canal section 21 transitions into a first resonance volume 22 starting from an end of the canal section 21 with a second diameter A2 that is wider than the first diameter A1, The acoustic canal 20 further comprises a second resonance volume 23 ending at one side in a second exterior opening 23a that receives the sound S. Another side of the second resonance volume 23 is separated from the first resonance volume 22 by a sound attenuating mesh 14 bouncing one side of each of the resonance volumes 22,23. The resonance volumes 22,23 may form part of respective resonance cavities C1,C2 separated by the mesh 14. The resonance cavities C1,C2 can thus provide resonance peaks R1,R2 that partially compensate attenuation of the mesh 14 in a resonance frequencies range Fr, e.g. above one kilohertz.

For the purpose of clarity and a concise description, features are described herein as part of the same or separate embodiments, however, it will be appreciated that the scope of the invention may include embodiments having combinations of all or some of the features described. Finally, the above-discussion is intended to be merely illustrative of the present systems and/or methods and should not be construed as limiting the appended claims to any particular embodiment or group of embodiments.

The invention claimed is:

1. An earplug for attenuating sound from an outside surroundings to an ear canal, the earplug comprising:
    a housing comprising an ear tip configured to form an acoustic seal with the ear canal; and
    an acoustic canal extending straight through the housing to guide the sound from the outside surroundings to inside the ear canal, the acoustic canal comprising:
        a canal section having a first diameter that is dimensioned to fit at least partially inside the ear canal, the canal section ending at one side in a first exterior opening that is in use directed to let the sound into the ear canal, wherein another side of the canal section transitions into
        a first resonance volume starting from an end of the canal section with a second diameter that is wider than the first diameter; the acoustic canal further comprising
        a second resonance volume with a third diameter that is wider than the second diameter and ending at one side in a second exterior opening that is in use directed to the outside surroundings for receiving the sound, wherein another side of the second resonance volume is separated from the first resonance volume by a sound attenuating mesh bounding one side of each of the resonance volumes;
    wherein the acoustic canal is directed along a straight line between the second exterior opening and the first exterior opening which is oppositely facing said second exterior opening;
    wherein a combined length of the canal section and the first resonance volume, measured between the sound attenuating mesh and an edge of the first exterior opening is between one and two centimeters;
    wherein a volume of the first resonance volume is larger than a volume of the canal section;
    wherein the first and second resonance volumes form at least part of respective first and second resonance cavities separated by the sound attenuating mesh;
    wherein the canal section and the first resonance volume are configured to form, in combination, the first resonance cavity with a first resonance peak for the sound in a first frequency range between two and five kilohertz;
    wherein the second resonance volume is configured to form the second resonance cavity with a second resonance peak for the sound in a second frequency range between five and ten kilohertz;

wherein the first and second resonance cavities are configured to provide the first and second resonance peaks that partially compensate attenuation of the sound attenuating mesh in a resonance frequencies range above one kilohertz.

2. The earplug according to claim 1, wherein the earplug comprises two parts that fit together with a controllable distance defining a variable volume of the first resonance cavity.

3. The earplug according to claim 1, wherein the acoustic canal is configured to provide at least the first and second resonance peaks that partially counteract attenuation of the sound by the sound attenuating mesh in respective frequency ranges around the at least the first and second resonance peaks.

4. The earplug according to claim 1, wherein maxima of the resonance peaks are at least two kilohertz apart.

5. The earplug according to claim 1, wherein the combined length of the canal section and first resonance volume, measured between the sound attenuating mesh and the edge of the first exterior opening is less than seventeen millimeter.

6. The earplug according to claim 1, wherein the second diameter is larger than the first diameter by a factor one-and-half or more.

7. The earplug according to claim 1, wherein the volume of the first resonance volume is larger than the volume of the canal section, by a factor one-and-half, or more.

8. The earplug according to claim 1, wherein a normal of the sound attenuating mesh is tilted at an angle with respect to a centerline of the acoustic canal for increasing its effective surface.

9. The earplug according to claim 1, wherein the second resonance volume is formed by a surrounding mantle section ending at one side with the sound attenuating mesh and at the opposite side in the second exterior opening to the outside surroundings, wherein the mantle section comprises one or more additional side openings to improve directional hearing.

10. The earplug according to claim 1, wherein the canal section is formed by a relatively narrow first tubular part covered by a flexible exterior configured to adapt its form to an entry of the ear canal, wherein the first resonance volume and second resonance volume are formed in a relatively wide second tubular part, wherein the second tubular part comprises the sound attenuating mesh separating the first resonance volume and second resonance volume, wherein the first and second tubular parts fit together to form the earplug.

11. A method for attenuating sound from an outside surroundings to an ear canal, the method comprising:

providing a housing comprising an ear tip to form an acoustic seal with the ear canal; and providing an acoustic canal extending straight through the housing to guide the sound from the outside surroundings to inside the ear canal, the acoustic canal comprising:

a canal section having a first diameter that fits at least partially inside the ear canal, the canal section ending at one side in a first exterior opening that lets the sound into the ear canal, wherein another side of the canal section transitions into a first resonance volume starting from an end of the canal section with a second diameter that is wider than the first diameter; the acoustic canal further comprising a second resonance volume with a third diameter that is wider than the second diameter and ending at one side in a second exterior opening that receives the sound, wherein another side of the second resonance volume is separated from the first resonance volume by a sound attenuating mesh bounding one side of each of the resonance volumes;

wherein the acoustic canal is directed along a straight line between the second exterior opening and the first exterior opening which is oppositely facing said second exterior opening;

wherein a combined length of the canal section and the first resonance volume, measured between the sound attenuating mesh and an edge of the first exterior opening is between one and two centimeters;

wherein a volume of the first resonance volume is larger than a volume of the canal section;

wherein the first and second resonance volumes form at least part of respective first and second resonance cavities separated by the sound attenuating mesh;

wherein the canal section and the first resonance volume are configured to form, in combination, the first resonance cavity with a first resonance peak for the sound in a first frequency range between two and five kilohertz;

wherein the second resonance volume is configured to form the second resonance cavity with a second resonance peak for the sound in a second frequency range between five and ten kilohertz;

wherein the first and second resonance cavities provide the first and second resonance peaks that partially compensate attenuation of the sound attenuating mesh in a resonance frequencies range above one kilohertz.

12. The method according to claim 11, further comprising providing a normal of the sound attenuating mesh tilted at an angle with respect to a centerline of the acoustic canal for increasing its effective surface.

* * * * *